(12) United States Patent
Layman et al.

(10) Patent No.: US 8,051,724 B1
(45) Date of Patent: Nov. 8, 2011

(54) LONG COOL-DOWN TUBE WITH AIR INPUT JOINTS

(75) Inventors: Frederick P. Layman, Carefree, AZ (US); Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 527 days.

(21) Appl. No.: 12/151,807

(22) Filed: May 8, 2008

Related U.S. Application Data

(60) Provisional application No. 60/928,946, filed on May 11, 2007.

(51) Int. Cl.
*G01N 1/22* (2006.01)

(52) U.S. Cl. .................................................. 73/863.21

(58) Field of Classification Search .............. 73/863.21, 73/863.81; 422/198, 200, 203, 228
See application file for complete search history.

(56) References Cited

U.S. PATENT DOCUMENTS

| | | | |
|---|---|---|---|
| 2,419,042 A | 4/1947 | Todd | 202/205 |
| 2,519,531 A | 8/1950 | Worn | 230/95 |
| 2,562,753 A | 7/1951 | Trost | 241/39 |
| 2,689,780 A | 9/1954 | Rice | 23/106 |
| 3,001,402 A | 9/1961 | Koblin | 73/421.5 |
| 3,067,025 A | 12/1962 | Chisholm | 75/616 |
| 3,145,287 A | 8/1964 | Siebein et al. | 219/75 |
| 3,178,121 A | 4/1965 | Wallace, Jr. | 241/5 |
| 3,179,782 A | 4/1965 | Matvay | 219/76.16 |
| 3,313,908 A | 4/1967 | Unger et al. | 219/76.16 |
| 3,401,465 A | 9/1968 | Larwill | 34/586 |
| 3,457,788 A | 7/1969 | Miyajima | 73/422 |
| 3,537,513 A | 11/1970 | Austin et al. | 165/70 |
| 3,741,001 A | 6/1973 | Fletcher et al. | 73/28 |
| 3,752,172 A | 8/1973 | Cohen et al. | 137/12 |
| 3,774,442 A | 11/1973 | Gustavsson | 73/28 |
| 3,830,756 A | 8/1974 | Sanchez et al. | 502/304 |
| 3,892,882 A | 7/1975 | Guest et al. | 427/446 |
| 3,914,573 A | 10/1975 | Muehlberger | 219/76.16 |
| 3,959,420 A | 5/1976 | Geddes et al. | 261/112 |
| 4,008,620 A | 2/1977 | Narato et al. | 73/421.5 A |

(Continued)

FOREIGN PATENT DOCUMENTS

JP    56-146804    11/1981

(Continued)

OTHER PUBLICATIONS

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670 &DOC=FILE.PDF., 6 pages.

(Continued)

*Primary Examiner* — Hezron Williams
*Assistant Examiner* — Tamiko D Bellamy
(74) *Attorney, Agent, or Firm* — Haverstock & Owens LLP (57) ABSTRACT

A conduit system comprising: a conduit formed by a surface extending from a first end to a second end, wherein the conduit is configured to channel a mixture stream from the first end to the second end; and a plurality of fluid delivery features disposed along the conduit between the first end and the second end, wherein each fluid delivery feature is configured to deliver a conditioning fluid into the conduit in an annular formation in a direction angled towards the second end in the same direction as the flow of the mixture stream, thereby providing a sheath of conditioning fluid between the conduit surface and the mixture stream.

21 Claims, 3 Drawing Sheets

U.S. PATENT DOCUMENTS

| | | | |
|---|---|---|---|
| 4,018,388 A | 4/1977 | Andrews | 241/39 |
| 4,139,497 A | 2/1979 | Castor et al. | |
| 4,157,316 A | 6/1979 | Thompson et al. | 502/304 |
| 4,171,288 A | 10/1979 | Keith et al. | |
| 4,174,298 A | 11/1979 | Antos | 502/230 |
| 4,248,387 A | 2/1981 | Andrews | 241/5 |
| 4,284,609 A | 8/1981 | deVries | |
| 4,388,274 A | 6/1983 | Rourke et al. | |
| 4,431,750 A | 2/1984 | McGinnis et al. | 502/329 |
| 4,436,075 A | 3/1984 | Campbell et al. | 123/557 |
| 4,505,945 A | 3/1985 | Dubust et al. | 427/8 |
| 4,513,149 A | 4/1985 | Gray et al. | |
| 4,731,517 A | 3/1988 | Cheney | 219/121.59 |
| 4,764,283 A | 8/1988 | Ashbrook et al. | 210/695 |
| 4,824,624 A | 4/1989 | Palicka et al. | 264/67 |
| 4,855,505 A | 8/1989 | Koll | |
| 4,866,240 A | 9/1989 | Webber | 219/121.47 |
| 4,983,555 A | 1/1991 | Roy et al. | 501/120 |
| 4,987,033 A | 1/1991 | Abkowitz et al. | 428/469 |
| 5,041,713 A | 8/1991 | Weidman | 219/121.51 |
| 5,043,548 A | 8/1991 | Whitney et al. | 219/121.84 |
| 5,070,064 A | 12/1991 | Hsu et al. | 502/325 |
| 5,073,193 A | 12/1991 | Chaklader et al. | 75/346 |
| 5,157,007 A | 10/1992 | Domesle et al. | 502/66 |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,439,865 A | 8/1995 | Abe et al. | |
| 5,442,153 A | 8/1995 | Marantz et al. | 219/121.47 |
| 5,460,701 A | 10/1995 | Parker et al. | 204/164 |
| 5,485,941 A | 1/1996 | Guyomard et al. | 222/1 |
| 5,534,149 A | 7/1996 | Birkenbeil et al. | |
| 5,553,507 A | 9/1996 | Basch et al. | 73/863.01 |
| 5,611,896 A | 3/1997 | Swanepoel et al. | 204/169 |
| 5,630,322 A | 5/1997 | Heilmann et al. | 62/95 |
| 5,726,414 A | 3/1998 | Kitahashi et al. | 219/121.8 |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |
| 5,811,187 A | 9/1998 | Anderson et al. | 428/403 |
| 5,837,959 A | 11/1998 | Muehlberger et al. | 219/121.47 |
| 5,851,507 A | 12/1998 | Pirzada et al. | |
| 5,853,815 A | 12/1998 | Muehlberger | 427/446 |
| 5,905,000 A | 5/1999 | Yadav et al. | 429/33 |
| 5,935,293 A | 8/1999 | Detering et al. | 75/10.29 |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,012,647 A | 1/2000 | Ruta et al. | 239/132.1 |
| 6,033,781 A | 3/2000 | Brotzman, Jr. et al. | 428/405 |
| 6,059,853 A | 5/2000 | Coombs | 75/332 |
| 6,102,106 A | 8/2000 | Manning et al. | 165/76 |
| 6,213,049 B1 | 4/2001 | Yang | 118/723 R |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,342,465 B1 | 1/2002 | Klein et al. | 502/339 |
| 6,344,271 B1 | 2/2002 | Yadav et al. | 428/402 |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,413,781 B1 | 7/2002 | Geis et al. | |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,548,445 B1 | 4/2003 | Buysch et al. | 502/230 |
| 6,554,609 B2 | 4/2003 | Yadav et al. | 432/9 |
| 6,562,495 B2 | 5/2003 | Yadav et al. | 429/12 |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,596,187 B2 | 7/2003 | Coll et al. | |
| 6,603,038 B1 | 8/2003 | Hagemeyer et al. | |
| 6,607,821 B2 | 8/2003 | Yadav et al. | 428/323 |
| 6,610,355 B2 | 8/2003 | Yadav et al. | 427/115 |
| 6,623,559 B2 | 9/2003 | Huang | 117/87 |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,710,207 B2 | 3/2004 | Bogan, Jr. et al. | 562/549 |
| 6,713,176 B2 | 3/2004 | Yadav et al. | 428/402 |
| 6,716,525 B1 | 4/2004 | Yadav et al. | 428/402 |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,855,426 B2 | 2/2005 | Yadav | 428/403 |
| 6,855,749 B1 | 2/2005 | Yadav et al. | 523/105 |
| 6,886,545 B1 | 5/2005 | Holm | 123/568.21 |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,527 B2 | 7/2005 | Boulos et al. | 219/121.52 |
| 6,933,331 B2 | 8/2005 | Yadav et al. | 523/210 |
| 6,986,877 B2 | 1/2006 | Takikawa et al. | 423/447.3 |
| 6,994,837 B2 | 2/2006 | Boulos et al. | 423/613 |
| 7,007,872 B2 | 3/2006 | Yadav et al. | 241/1 |
| 7,022,305 B2 | 4/2006 | Drumm et al. | |
| 7,052,777 B2 | 5/2006 | Brotzman, Jr. et al. | 428/570 |
| 7,073,559 B2 | 7/2006 | O'Larey et al. | 164/76.1 |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,172,790 B2 | 2/2007 | Koulik et al. | 427/212 |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 7,417,008 B2 | 8/2008 | Richards et al. | 502/306 |
| 7,494,527 B2 | 2/2009 | Jurewicz et al. | 75/346 |
| 7,541,012 B2 | 6/2009 | Yeung et al. | 423/245.1 |
| 7,572,315 B2 | 8/2009 | Boulos et al. | 75/336 |
| 7,611,686 B2 | 11/2009 | Alekseeva et al. | |
| 7,615,097 B2 | 11/2009 | McKechnie et al. | 75/346 |
| 7,622,693 B2 | 11/2009 | Foret | 219/121.43 |
| 7,803,210 B2 | 9/2010 | Sekine et al. | 75/334 |
| 2001/0042802 A1 | 11/2001 | Youds | 241/5 |
| 2002/0068026 A1 | 6/2002 | Murrell et al. | |
| 2002/0079620 A1 | 6/2002 | DuBuis et al. | 264/328.14 |
| 2002/0143117 A1 | 10/2002 | Ito et al. | 700/95 |
| 2002/0182735 A1 | 12/2002 | Kibby et al. | 436/37 |
| 2003/0036786 A1 | 2/2003 | Duren et al. | 607/96 |
| 2003/0042232 A1 | 3/2003 | Shimazu | |
| 2003/0066800 A1 | 4/2003 | Saim et al. | |
| 2003/0108459 A1 | 6/2003 | Wu et al. | 422/186.04 |
| 2003/0139288 A1 | 7/2003 | Cai et al. | 502/303 |
| 2003/0172772 A1 | 9/2003 | Sethuram et al. | |
| 2003/0223546 A1 | 12/2003 | McGregor et al. | 378/143 |
| 2004/0009118 A1 | 1/2004 | Phillips et al. | |
| 2004/0023302 A1 | 2/2004 | Archibald et al. | 506/12 |
| 2004/0023453 A1 | 2/2004 | Xu et al. | |
| 2004/0103751 A1 | 6/2004 | Joseph et al. | 75/10.19 |

| | | | | |
|---|---|---|---|---|
| 2004/0119064 A1 | 6/2004 | Narayan et al. .................... 7/14 | | |
| 2004/0127586 A1 | 7/2004 | Jin et al. ......................... 518/715 | | |
| 2004/0167009 A1 | 8/2004 | Kuntz et al. ................... 501/95.2 | | |
| 2004/0176246 A1 | 9/2004 | Shirk et al. ..................... 502/439 | | |
| 2004/0213998 A1 | 10/2004 | Hearley et al. ................. 428/402 | | |
| 2004/0251017 A1 | 12/2004 | Pillion et al. .................. 165/289 | | |
| 2005/0000321 A1 | 1/2005 | O'Larey et al. ................. 75/952 | | |
| 2005/0000950 A1 | 1/2005 | Schroder et al. ......... 219/121.59 | | |
| 2005/0077034 A1 | 4/2005 | King ............................ 165/163 | | |
| 2005/0097988 A1 | 5/2005 | Kodas et al. .................... 75/332 | | |
| 2005/0199739 A1 | 9/2005 | Kuroda et al. | | |
| 2005/0220695 A1 | 10/2005 | Abatzoglou et al. | | |
| 2005/0233380 A1 | 10/2005 | Pesiri et al. ..................... 435/7.1 | | |
| 2005/0240069 A1 | 10/2005 | Polverejan et al. ........... 585/444 | | |
| 2005/0258766 A1 | 11/2005 | Kim .......................... 315/111.21 | | |
| 2006/0051505 A1 | 3/2006 | Kortshagen et al. .......... 427/212 | | |
| 2006/0068989 A1 | 3/2006 | Ninomiya et al. | | |
| 2006/0094595 A1 | 5/2006 | Labarge ........................ 502/325 | | |
| 2006/0096393 A1 | 5/2006 | Pesiri ......................... 73/863.21 | | |
| 2006/0105910 A1 | 5/2006 | Zhou et al. | | |
| 2006/0108332 A1 | 5/2006 | Belashchenko .......... 219/121.47 | | |
| 2006/0153728 A1 | 7/2006 | Schoenung et al. | | |
| 2006/0153765 A1 | 7/2006 | Pham-Huu et al. ........... 423/345 | | |
| 2006/0159596 A1 | 7/2006 | De La Veaux et al. ........ 422/151 | | |
| 2006/0231525 A1 | 10/2006 | Asakawa et al. ................ 216/56 | | |
| 2007/0048206 A1 | 3/2007 | Hung et al. .................... 423/335 | | |
| 2007/0063364 A1 | 3/2007 | Hsiao et al. ....................... 264/5 | | |
| 2007/0084308 A1 | 4/2007 | Nakamura et al. ............. 75/346 | | |
| 2007/0084834 A1 | 4/2007 | Hanus et al. ............... 219/121.5 | | |
| 2007/0087934 A1 | 4/2007 | Martens et al. ............... 502/214 | | |
| 2007/0173403 A1 | 7/2007 | Koike et al. | | |
| 2007/0253874 A1 | 11/2007 | Foret ........................ 422/186.07 | | |
| 2007/0292321 A1* | 12/2007 | Plischke et al. ............... 422/198 | | |
| 2008/0031806 A1 | 2/2008 | Gavenonis et al. ........... 423/606 | | |
| 2008/0038578 A1 | 2/2008 | Li ................................. 428/627 | | |
| 2008/0064769 A1 | 3/2008 | Sato et al. ..................... 518/717 | | |
| 2008/0105083 A1 | 5/2008 | Nakamura et al. ............. 75/255 | | |
| 2008/0116178 A1 | 5/2008 | Weidman | | |
| 2008/0206562 A1 | 8/2008 | Stucky et al. ................. 428/403 | | |
| 2008/0274344 A1 | 11/2008 | Vieth et al. ................. 438/304.4 | | |
| 2009/0010801 A1 | 1/2009 | Murphy et al. ................... 422/4 | | |
| 2009/0088585 A1 | 4/2009 | Schammel et al. ........... 562/409 | | |
| 2009/0114568 A1 | 5/2009 | Trevino et al. ................ 208/139 | | |
| 2009/0162991 A1 | 6/2009 | Beneyton et al. ............. 438/455 | | |
| 2009/0168506 A1 | 7/2009 | Han et al. ...................... 365/171 | | |
| 2009/0181474 A1 | 7/2009 | Nagai ............................... 438/3 | | |
| 2009/0274903 A1 | 11/2009 | Addiego ....................... 428/337 | | |
| 2009/0286899 A1 | 11/2009 | Hofmann et al. ............... 522/99 | | |

FOREIGN PATENT DOCUMENTS

| | | |
|---|---|---|
| JP | 7031873 A | 2/1995 |
| SU | 493241 | 3/1976 |
| WO | WO 02/092503 A1 | 11/2002 |
| WO | 2004052778 A2 | 6/2004 |
| WO | WO 2006/079213 A1 | 8/2006 |

OTHER PUBLICATIONS

J. Heberlein, "New Approaches in Thermal Plasma Technology", Pure Appl. Chem., vol. 74, No. 3, 2002, pp. 327-335.

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I Ii, P. Fauchais, Universite de Limoges, 123 Avenue A. Thomas 87000, Limoges, F. , Pure & Chem, vol. 68, No. 5, pp. 1093-1099, 1996.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M. Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

Nagai, Yasutaka, et al., "Sintering Inhibition Mechanism of Platinum Supported on Ceria-based Oxide and Pt-oxide-support Interaction," Journal of Catalysis 242 (2006), pp. 103-109, Jul. 3, 2006, Elsevier.

Kenvin et al. "Supported Catalysts Prepared from Monouclear Copper Complexes: Catalytic Properties", Journal of Catalysis, pp. 81-91, 1992.

National Aeronautics and Space Administration, "Enthalpy", http://www.grc.nasa.gov/WWW/K-12/airplane/enthalpy.html, Nov. 23, 2009, 1 page.

Derwent English Abstract for publication No. SU 193241 A, Application No. 1973SU1943286 filed on Jul. 2, 1973, published on Mar. 1, 1976, entitled "Catalyst for Ammonia Synthesis Contains Oxides of Aluminium, Potassium, Calcium, Iron and Nickel Oxide for Increased Activity," 3 pgs.

* cited by examiner

LONG COOL-DOWN TUBE WITH AIR INPUT JOINTS

CROSS-REFERENCE TO RELATED APPLICATIONS

The present application claims to co-pending U.S. Provisional Application Ser. No. 60/928,946, filed May 11, 2007, entitled "MATERIAL PRODUCTION SYSTEM AND METHOD," which is hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE PRESENT INVENTION

The present invention relates to methods of cooling and controlling the flow of a hot, reactive medium containing gas or vapor phase particles.

BACKGROUND OF THE PRESENT INVENTION

Gas or vapor phase particle production is an important technique for producing engineered materials, especially nanomaterials. Specific characteristics of particles produced in gas or vapor phase synthesis reactions depend not only on the energy delivered to the reactive medium, but also on the conditioning of the reactive medium once the medium has left the reactor.

In a particle production reactor, basic product species are formed within extremely short time spans as the reactive medium cools following ejection from the energy delivery zone. During the time following ejection, further formation mechanisms determine the ultimate characteristics of the final product.

Chemical reactions such as nucleation and surface growth occur within precursor materials largely during energy delivery. However, these formation mechanisms continue to be active in the first short moments following ejection. More prevalent in the post-ejection time period are bulk formation mechanisms, such as coagulation and coalescence, which operate on already formed particles. Proper conditioning of the reactive medium following ejection from the energy delivery zone accounts for these and other formation mechanisms to control formation of a final product having desired characteristics.

In addition to particle formation, proper conditioning must account for post-formation processing of the product. Although particles, once formed, cool rapidly through radiative heat loss, the residual gas in which they are entrained after formation cools much more slowly, and especially so when confined. Confinement is necessary to some degree in any controlled-environment processing system, and economic concerns usually dictate relatively confining controlled environments because large environments cost more to build and maintain. Because supply systems require product sufficiently cool for handling, such systems must provide efficient mechanisms for cooling of the entire gas-particle product, yet also provide for efficient transport of the product to collection points within the system. They must also prevent agglomeration of the particles beyond a certain point or time period to ensure proper grain size in the final product.

Transport of particles within a gas stream relies on entrainment of the particle, which is largely a function of particle properties, including mass, temperature, density, and interparticle reactivity, as well as gas properties, including density, velocity, temperature, viscosity, and composite properties, such as particle-gas reactivity. Cooling of a gas by definition affects gas temperature, but also may easily lead to changes in other properties listed above, exclusive of mass. In view of this, balancing efficient cooling and transport of gas-particle product requires careful optimization of process parameters, which the present invention seeks to achieve.

SUMMARY OF THE PRESENT INVENTION

According to the present invention, a conduit system for transporting particle and gas mixtures is presented. The conduit system is primarily intended to condition and conduct gas particle product emitted from gas phase particle production reactors, such as flame reactors, plasma reactors, hot wall reactors and laser reactors. Conditioning performed within the system includes cooling of gas-vapor mixtures and maintaining entrainment of particles therein for sampling and collection. The conditioning performed within the present invention accounts for particle interaction mechanisms within the gas particle mixture.

The conduit system comprises a conduit defining a flow direction from a first end to a second end and including a plurality of fluid delivery features. The fluid delivery features each include a port in the interior surface of the conduit, and are spaced along the conduit. The ports allow communication between the exterior and the interior of the conduit.

The conduit system works to cool, deliver and further condition a reactive gas-particle mixture produced by a gas phase particle production reactor. In operation, a hot gas-particle mixture tends to expand as it flows through the conduit. Expansion of the gas-particle mixture against the inner surfaces of the conduit can lead to adhesion thereto by particles and subsequently to the deposit of residues within the conduit. This pollution of the conduit can affect fluid flow within the conduit and can contaminate subsequent gas-particle mixtures flowing in the conduit.

The occurrence of significant deposits would make regular cleaning of the conduit necessary to ensure proper operation. Cleaning can require deactivation of the equipment and reduce the efficiency of the process, thereby resulting in increased expense and decreased productivity.

However, occurrence of residue is minimized by the present invention, in which conditioning fluid flows into the conduit through the plurality fluid delivery features, providing a sheath of conditioning fluid between the gas-particle mixture and the inner surfaces of the conduit. Preferably, the conditioning fluid flows symmetrically through one or more ports into the conduit. Symmetric inflow of conditioning fluid constricts the flow of the gas-particle mixture and reinforces the conditioning fluid sheath in the region of each fluid delivery feature. Preferably, fluid delivery features provide conditioning fluid regularly enough so that complete intermixture of the gas-particle mixture with the conditioning fluid sheath never occurs. The conditioning fluid is preferably provided at a cooler temperature than the gas-particle mixture and substantially prevents the gas-particle mixture from encountering the inner surfaces of the conduit. In a further aspect, the temperature of the region of the conduit surrounding each fluid delivery feature can be controlled to aid in conditioning the gas-particle mixture and to prevent deposition of particles thereon.

A specific conditioning fluid is selected for its intrinsic properties. Desired intrinsic properties depend to an extent on the specific mixture being conducted through the conduit. For example, typically inert gasses, such as argon, neon, and
} helium, are preferred for their near-non existent reactivity. Among inert gasses, argon is more preferred than helium or neon because it provides a more effective sheath. Furthermore, extrinsic properties, such as temperature and density, correlate to the ability of the conditioning fluid to cool and condition the gas-particle mixture and are controlled to provide desired levels of cooling and conditioning to the gas-particle mixture.

Although the specific mixture under consideration partially determines the conditioning fluid used and the selection of the extrinsic fluid properties, the location of fluid introduction also must be considered. In one embodiment, the conditioning fluid introduced through the features closer to the particle source is different than the fluid introduced through the features farther from the particle source. For example, a first gas can be introduced through the features closer to the injection end of the conduit, while a second gas can be introduced through the features farther away from the injection end. In alternative embodiments, the same type of conditioning fluid is introduced through each fluid delivery feature, but extrinsic properties of the fluid, such as temperature, are varied according to the delivery location. The conditioning fluid introduced through each feature in the set of fluid introduction features is preferably chosen to balance the competing concerns of economic efficiency and high product quality. Preferably, the conditioning fluid is supplied passively, as described more fully below, through a neutral pressure environment formed around fluid delivery ports within the conduit. Furthermore, the conduit is configured so that the conditioning fluid flows at a rate sufficient to maintain entrainment of the particles within the gas flow.

Therefore, the present invention provides a flowing sheath of conditioning gas along the inner walls of a conduit through which a gas-particle mixture flows. As the conditioning gas and the gas-particle mixture flow through the conduit, the introduction of fresh conditioning gas maintains entrainment of the particles and cools the gas-particle mixture.

In one aspect of the present invention, a conduit system is provided. The conduit is formed by a surface extending from a first end to a second end. The conduit is configured to channel a mixture stream from the first end to the second end. A plurality of fluid delivery features are disposed along the conduit between the first end and the second end. Each fluid delivery feature is configured to deliver a conditioning fluid into the conduit in an annular formation in a direction angled towards the second end in the same direction as the flow of the mixture stream, thereby providing a sheath of conditioning fluid between the conduit surface and the mixture stream.

In another aspect of the present invention, a method of conditioning a mixture stream is provided. The method comprises providing a conduit formed by a surface extending from a first end to a second end. A plurality of fluid delivery features are disposed along the conduit between the first end and the second end. The mixture stream flows through the conduit from the first end to the second end. A conditioning fluid is delivered into the conduit while the mixture stream flows through the conduit. The conditioning fluid is delivered through a plurality of delivery features disposed along the conduit between the first end and the second end. Each fluid delivery feature delivers the conditioning fluid into the conduit in an annular formation in a direction angled towards the second end in the same direction as the flow of the mixture stream, thereby providing a sheath of conditioning fluid between the conduit surface and the mixture stream.

In preferred embodiments, each fluid delivery feature comprises a ports structure and an annular housing. The port structure is fluidly coupled to the interior of the conduit and is configured to deliver the conditioning fluid into the conduit in an annular formation in a direction angled towards the second end in the same direction as the flow of the mixture stream. The annular housing is disposed around the conduit and covers the port structure. The annular housing comprises a fluid supply port configured to supply the conditioning fluid to the port structure for delivery into the conduit.

DETAILED DESCRIPTION OF THE INVENTION

The description below concerns several embodiments of the invention. The discussion references the illustrated preferred embodiment. However, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders(nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accompanying drawings. To facilitate this description, like reference numerals designate like elements.

The present invention includes a plurality of fluid delivery features. Each fluid delivery feature preferably includes one or more ports configured to deliver a symmetrical sheath of conditioning fluid. Although the specific details of the fluid delivery features are determined within each embodiment, largely with reference to the types of fluids and particles the embodiment is designed to deal with, the generally preferred configuration of the ports is discussed in the following paragraphs. Furthermore, the operation of the fluid delivery features and the effect of fluid and particle parameters on their design are also discussed.

The ports allow communication between the exterior and the interior of the conduit. Preferably, each port is configured to deliver conditioning fluid evenly and along the inner surface of the conduit substantially in the direction of flow within the conduit. Two structural features are preferably present in each fluid delivery feature: the ports are angled along the flow direction of the conduit, and each port delivers fluid along the entirety of an inner cross-sectional boundary of the conduit. Fluid can be delivered evenly or unevenly along the entirety of the inner cross-sectional boundary. In one embodiment, uneven fluid delivery is used to counteract the influence of gravity on the entrained particles.

The first structural feature results in an angled path of fluid flow into the conduit through the ports. Introducing conditioning fluid along an angled path results in less significant disturbances to the gas-particle mixture flowing through the interior 'core' of the conduit, resulting in little additional turbulence therein. As discussed below, less significant perturbation of the gas-particle mixture results in less efficient cooling, but succeeds in minimizing particle deposition within the conduit. Although a less-angled path of fluid flow more parallel to the direction of flow within the conduit may be preferred in some applications, the present invention prefers an angular path of delivery to allow for constriction of the gas-particle mixture flow.

The second preferred structural feature, each port delivering fluid along the entirety or substantial entirety of an inner cross-sectional boundary of the conduit, seeks to maximize effectiveness of the conditioning gas as a sheath between the gas-particle mixture and the inner surface of the conduit. The present invention contemplates myriad ways of accomplishing this goal. In one aspect, each port is formed from a plurality of sub-ports, each shaped to provide fluid flow along a small portion of the inner surface. The sub-ports are tapered, offset or otherwise situated so that sufficient material remains within the conduit to provide structural stability around the port. In a further aspect, one continuous port is provided within the inner surface of the conduit and an external housing is coupled to the conduit to provide structural support in the region of the port. In this aspect, the housing may also provide a fluid reservoir where conditioning fluid is held and allowed to flow into the port.

Furthermore, each port is preferably in fluid communication with a reservoir containing conditioning fluid. In the preferred embodiment of the present invention, the reservoir is integrated into a housing surrounding a port of a fluid delivery feature in the conduit. In this aspect, the housing provides structural support to the conduit. In alternative embodiments, the reservoir is simply a manifold for conditioning fluid delivery and does not provide structural support to the conduit. In a further alternative embodiment, the reservoir is a chamber sealed with the conduit and surrounding a structural housing including a fluid supply port. In each aspect, the reservoir is sealed to the conduit. Exemplary seals include high temperature o-ring seals, pressure fitted seals, and integral constructions.

Conditioning fluid is preferably supplied to the reservoir through a supply port exposed to the reservoir. The reservoir preferably has the smallest possible volume while still maintaining sufficient space therein to allow uninterrupted flow of conditioning fluid into the conduit, so long as conditioning fluid is maintained at appropriate pressure, as will be discussed more fully below. In alternative embodiments, conditioning fluid is supplied directly from a fluid manifold to the port, or to each sub-port where the port comprises more than one sub-port with no intervening reservoir.

The present invention contemplates a variety of constructions for the conduit system, including fully modular constructions, fully integrated constructions, and combinations thereof. In an exemplary modular construction, the conduit system is pieced together from a plurality of components, each belonging to one of two component types: conduit pieces, and couplers.

The conduit pieces contemplated are simply lengths of conduit having substantially constant cross sectional dimensions. Preferably these conduit pieces have lengths substantially greater than their cross-sectional dimensions. Furthermore, these conduit pieces are preferably actively cooled by a heat exchanger.

Couplers join multiple conduit pieces together. Preferably, two adjacent conduit pieces are joined by one coupler. The couplers include the fluid delivery features mandated in the present invention. Specifically, a modular conduit coupler comprises a first and a second end each configured to couple with a conduit piece. Between the first and second ends, one or more ports are formed to deliver fluid into the coupler. Furthermore, a fluid reservoir is preferably coupled with the one or more ports formed in the coupler. In an additional aspect, the one or more ports can have a variable total surface area.

In one particular embodiment, a coupler comprises two cylindrical pieces with substantially similar outer cross-sectional dimensions and each having one chamfered edge configured so that the chamfered edges are mateable and positioned a gap distance from one another to form a gap therebetween. The coupler also comprises a third cylindrical piece configured to mate with the exterior surfaces of the two cylindrical pieces to effectively couple the two pieces with one another such that the third cylindrical piece covers the gap, the third piece has a passageway therein for supplying fluid to the gap. Furthermore, the third piece can be slidably configured to adjust the total surface area of the gap, and thus adjust the flow volume of conditioning fluid into the conduit.

Preferably, the conduit has the following general dimensional characteristics. The spacing between the fluid delivery features is substantially larger than the cross-sectional dimension of the conduit, and the outer cross-sectional dimension of the conduit is substantially constant over its length. Furthermore, the fluid delivery features are preferably spaced evenly along the conduit. However, the present invention contemplates other spacings.

In a preferred embodiment, the ratio between the cross-sectional dimension and the fluid delivery spacing is approximately 1 to 36. More specifically, the conduit preferably has a cross-sectional dimension of approximately 2 inches, and the preferable spacing between fluid delivery features is approximately 6 feet.

As described above, a purpose of regularly introducing conditioning gas is to maintain entrainment of particles within the gas-particle mixture and to prevent deposition of particles on the surfaces of the conduit. The likelihood of particle deposition within the conduit increases as intermixture of the gas-particle mixture with the sheath of conditioning gas occurs. Ideally, the gas-particle mixture is confined to the inner 'core' of the conduit. Preferably, the sheath of conditioning gas surrounds the gas-particle mixture 'core' and insulates the conduit surfaces from interaction with particles. Without regular introduction of conditioning gas, particle deposits within the conduit may occur. The specific regularity of introduction necessary is largely determined by the particular gas-particle mixture. Conduit systems in accordance with the present invention differ in the spacing of their fluid delivery features according to the gas-particle mixture for which they are designed, and in other aspects as well. Furthermore, the extrinsic properties, e.g., temperature and pressure, of the conditioning gas are controlled to maintain entrainment of the particles within the gas-particle mixture.

In the present invention, the spacing between fluid delivery features is determined with a goal of preventing full intermixture between the conditioning gas sheath and the gas-particle mixture at any point in the conduit. Intermixture between the gas-particle mixture and the conditioning gas depends on many factors including temperature, particle properties, density, velocity, viscosity, both of the mixture and of the conditioning gas.

Another aspect of conduit system design directed to maintaining particle entrainment is the spacing of the fluid delivery features. Regular introduction of fresh conditioning gas is preferred to maintain integrity of the sheath of conditioning gas. As the gas-particle mixture and surrounding sheath of conditioning gas travel away from a fluid delivery feature, they tend to intermix: increasing intermixture of the sheath gas and the core of gas-particle mixture leads to undesired interactions between the particles and the surfaces of the conduit.

Figure 2:
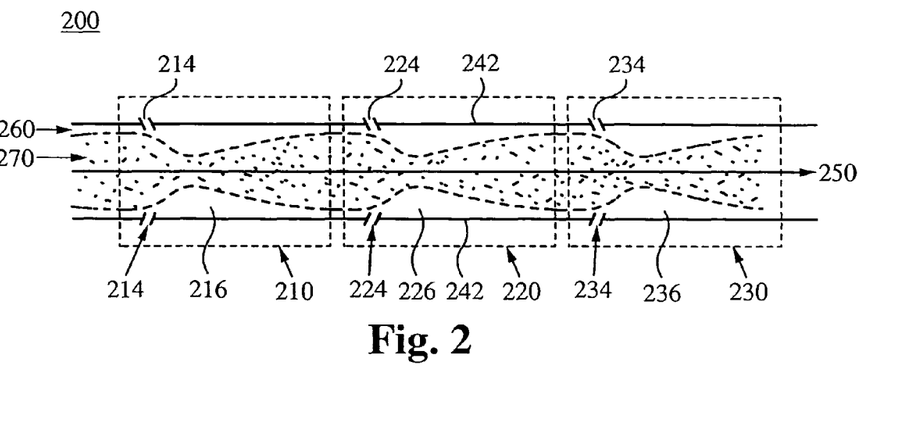
FIG. 2 is a schematic cross-sectional view of one embodiment of a conduit system in accordance with the principles of the present invention.

Although, as described above, regular introduction of conditioning fluid is preferred within the present invention, the inclusion of multiple different spacings is also contemplated. As described earlier, the conditioning fluid sheath loses integrity and stops functioning due to intermixture of the gas-particle mixture and the sheath. When the temperature difference between the conditioning gas sheath and the gas-particle mixture is greater, the two fluids mix more rapidly, e.g., within a shorter distance of conduit, following introduction of the conditioning fluid. Therefore, because the particle-gas mixture cools as it flows through the conduit, the frequency of introduction for some systems can be lessened farther along the conduit in the direction of flow. In other words, the spacing of the fluid delivery features can increase along the conduit in the direction of flow.

The flow of the conditioning gas into the fluid delivery features is preferably caused by formation of a negative pressure differential along the conduit, which also aids in maintaining flow of the mixture within the conduit. This negative pressure differential is preferably formed by coupling a vacuum formation system with the end of the conduit. Alternatively, the negative pressure differential is formed by drawing fluid from a distal end of the conduit. In further alternative embodiments, active injection of conditioning fluid is contemplated.

Furthermore, the conduit is preferably engineered so that any deposition of particles within the conduit will be relatively permanent with respect to the gas-particle stream. In other words, no significant variation in stream flow rate or strength occurs whereby an earlier-deposited particle might be re-entrained into the stream. Substantially constant fluid flow rates also promote more ‘permanent’ deposition. Accordingly, operation of the vacuum system or other flow control system must be carefully controlled.

Referring now to FIG. 1A, a particle processing system 100 incorporates an embodiment of the present invention. The particle processing system 100 preferably includes a gas-particle mixture production system 110 fluidly coupled with a vacuum system 160 through a conduit system 120. In a preferred embodiment, a sampling zone 150 is fluidly coupled between the conduit system 120 and the vacuum system.

Some embodiments of the present invention revolve around the use of a nano-powder production reactor. In general, vapor phase nano-powder production means are preferred. The mixture production system 110 can use elements of nano-powder production systems similar to those disclosed in U.S. patent application Ser. No. 11/110,341, filed on Apr. 19, 2005 and entitled, “HIGH THROUGHPUT DISCOVERY OF MATERIALS THROUGH VAPOR PHASE SYNTHESIS”, which is currently published as U.S. Publication No. 2005-0233380-A. In such a nano-powder production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas.

Referring back to FIG. 1A, the gas-particle mixture production system 110 preferably produces particles entrained within a gas stream and provides the output mixture stream to the conduit system 120. The gas-particle mixture flows through the conduit 140 of the conduit system 120, where it is conditioned and conducted to the sampling zone 150. Within the sampling zone 150 portions of the gas-particle mixture are separated and the particles therein isolated for further analysis. The bulk of the gas-particle mixture flows through the sampling zone and into the vacuum system 160. The vacuum system 160 functions to draw the gas-particle mixture from the production system 110 through the conduit system 120, forcing it through the sampling zone 150.

The conduit system 120 conducts and processes the gas-particle mixture, maintaining entrainment of particles within the mixture by both physically processing the mixture and by surrounding the mixture with a conditioning fluid sheath. Aspects of the physical processing performed by the conduit system 120 are discussed in more detail later in this paper. To form a sheath around the gas-particle mixture, the conditioning fluid is provided through a plurality of port structures 141, 143, and 145 formed within the conduit 140. In a preferred embodiment, a conditioning fluid reservoir system 130 delivers conditioning fluid through the fluid delivery lines 132, 134, and 136 to the respective conditioning fluid delivery chambers 142, 144, and 146 of the conduit structure 120. The conditioning fluid delivery chambers 142, 144, and 146 respectively surround the port structures 141, 143, and 145. In one embodiment of the present invention, the fluid reservoir system 130 comprises a single fluid reservoir containing a single type of conditioning fluid which flows through each of the fluid delivery lines 132, 134, and 136. In alternative embodiments, the fluid delivery structure comprises multiple reservoirs, each containing possibly different types of conditioning fluid that are delivered through the conditioning fluid lines 132, 134, and 136 to the conditioning fluid delivery chambers 142, 144, and 146 respectively. As described earlier, in some instances the present invention contemplates varying both the type, and the physical properties of the conditioning gas based on the location of the fluid delivery port under consideration. The various embodiments of the conditioning fluid delivery system 130 are configured based on the type of variation desired.

In one embodiment, the fluid delivery chambers 142, 144, and 146 are disposed within housings that provide structural support to the conduit 140. In alternative embodiments, the fluid delivery chambers 142, 144, and 146 are sealed reservoirs that do not provide structural support to the conduit 140, but instead, the port structures 141, 143, and 145 comprise structural elements. In either case, the fluid delivery chambers 142, 144, and 146 are preferably sealed with the conduit 140 via bonding, pressure fitting, integral formation, or construction using a high temperature o-ring seal.

Figure 1A:
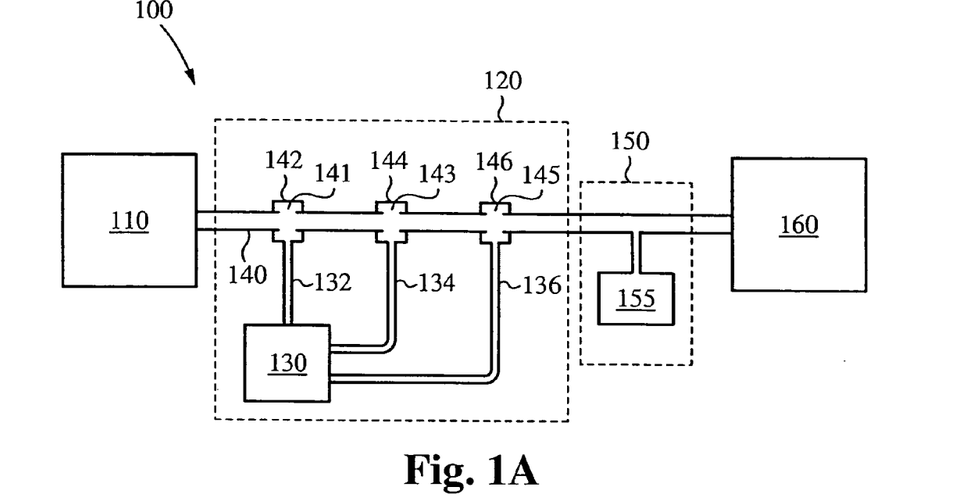
FIGS. 1A and 1B are systematic views of two embodiments of a conduit system integrated into particle processing systems in accordance with the principles of the present invention.
Figure 1B:
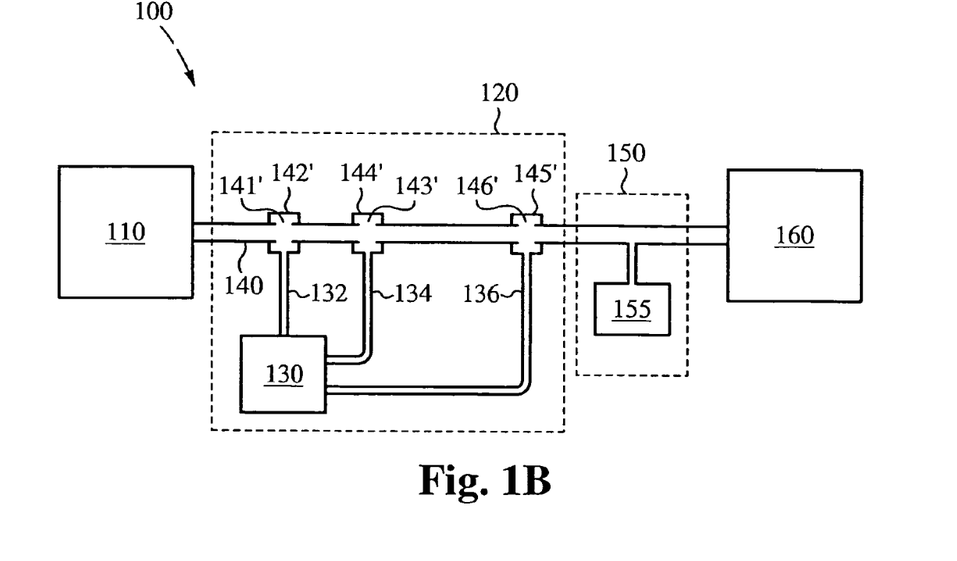
Figure 3:
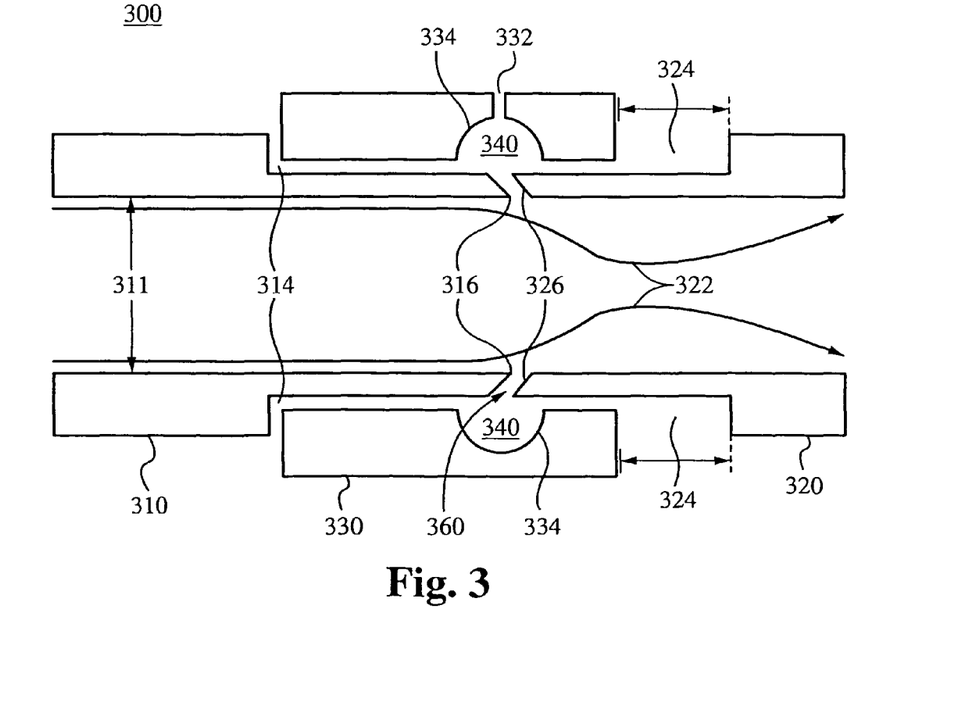
FIG. 3 is a cross-sectional view of one embodiment of a conduit coupler in accordance with the principles of the present invention.

The repeated introduction of conditioning gas, combined with the length of travel from the production system 110 and the physical processing discussed more thoroughly elsewhere, combine to cool and conduct the gas to the sampling zone 150, while maintaining entrainment and minimizing deposition of the particles within the conduit system 120. The sampling zone 150 includes the sampling device 155 coupled with the conduit system 120 to separate a portion of a gas-particle mixture flowing therein. In aspects of the present invention, the sampling device 155 has an optimal operating temperature range for the sampled gas-particle mixture. Preferably, the conduit system 120 and the sampling zone 150 are configured to cool the gas-particle mixture to within the optimal operating temperature range of input for the sampling device 155. Configuration parameters for the conduit system 120 include overall distance from the production system 110 to the sampling zone 150, the number and frequency of ports, and the type of conditioning gas introduced into the ports.

It is contemplated that the sampling device 155 can be configured in a variety of ways. In one embodiment, the sampling device 155 comprises a sampling structure, at least one filled aperture formed in the sampling structure, and at least one unfilled aperture formed in the sampling structure. Each filled aperture is configured to collect particles from the mixture stream, such as by using a filter. The sampling structure is configured to be adjusted between a pass-through configuration and a collection configuration. The pass-through configuration comprises an unfilled aperture being fluidly aligned with a conduit, such as conduit 140, thereby allowing the unfilled aperture to receive the mixture stream from the conduit and the mixture stream to flow through the sampling structure without substantially altering the particle content of the mixture stream. The collection configuration comprises a filled aperture being fluidly aligned with the conduit, thereby allowing the filled aperture to receive the mixture stream and collect particles while the mixture stream is being flown through the filled aperture.

It is contemplated that the sampling structure can be adjusted between the pass-through configuration and the collection configuration in a variety of ways. In one embodiment, the sampling structure is a disk-shaped structure including an annular array of apertures, wherein the annular array comprises a plurality of the filled apertures and a plurality of the unfilled apertures. The sampling structure is rotatably mounted to a base, wherein rotational movement of the sampling structure results in the adjustment of the sampling structure between the pass-through configuration and the collection configuration. In another embodiment, the sampling structure is a rectangular-shaped structure including a linear array of apertures, wherein the linear array comprises a plurality of the filled apertures and a plurality of the unfilled apertures. The sampling structure is slideably mounted to a base, wherein sliding of the sampling structure results in the adjustment of the sampling structure between the pass-through configuration and the collection configuration.

As shown in FIG. 1A, the fluid delivery chambers 142, 144, and 146 can be regularly spaced. However, the fluid delivery chambers of the present invention need not be evenly spaced. For example, in FIG. 1B, the fluid delivery chambers 142', 144', and 146' are unevenly spaced. Preferably, the spacing of the fluid delivery chambers is determined with reference to the type of gas-particle mixture the conduit system 120 is designed to conduct. As discussed more fully below, the frequency of introduction of conditioning gas relates to the maintenance of entrainment of particles within the gas-particle mixture.

Referring now to FIG. 2, the physical processing of a conducted gas-particle mixture by a conduit system in accordance with the present invention is discussed. A conduit system 200 includes a plurality of fluid delivery features 210, 220, and 230. In a preferred embodiment, the fluid delivery features are fluidly coupled with one or more fluid reservoirs (not shown) containing conditioning fluid as described and shown earlier with reference to FIG. 1.

Each fluid delivery feature 210, 220, 230 preferably includes a port structure 214, 224, 234 with which a fluid reservoir is coupled to introduce conditioning fluid into the conditioning fluid stream 260 within the conduit structure 200 as described above. The introduction of conditioning fluid in a symmetric distribution from the port structures 214, 224, 234 around the gas-particle mixture stream 270 causes constriction of the gas-particle mixture stream 270 at the constriction points 216, 226, 236. After the constriction of the gas particle mixture stream 270, the mixture stream 270 will begin to mix with the conditioning fluid stream 260 and expand toward the interior wall of the conduit 242 after a period of time. Preferably, the next port structure will constrict the gas-particle mixture stream 270 before it expands to completely fill the conduit 242. Both the conditioning fluid stream 260 and the gas-particle mixture stream 270 flow in the direction of the arrow 250. The motive force determining this flow direction is preferably an external low pressure source, such as a vacuum as discussed elsewhere. However, it is contemplated that the motive force can be provided in other ways as well.

As the gas-particle mixture 270 flows through the fluid delivery features 210, 220, 230, the conditioning fluid delivery promotes entrainment of particles within the flowing mixture 270 and prevents contamination of conduit system 200. By providing an insulating layer between the gas-particle mixture and the inner surfaces of the conduit system 200, delivery of conditioning fluid substantially prevents deposition thereon of particles and subsequent contamination.

As mentioned earlier, if deposition does occur, the configuration of fluid delivery features 210, 220, 230, combined with substantially constant fluid flow, substantially prevents deposited content from re-entraining into the flow of fluid within the conduit system 200. Thus, under desired operating conditions, particles do not reenter the stream once deposited.

Although the fluid delivery features 210, 220, and 230 appear substantially identical as illustrated, the present invention contemplates modifying the shapes and configurations thereof according to their relative spacing along the flow direction of the conduit system 200.

Referring now to FIG. 3, one embodiment of a conduit coupler 300 incorporates a fluid delivery feature in accordance with the present invention. The conduit coupler 300 comprises three subsections 310, 320, and 330. In a preferred embodiment, the conduit subsections 310 and 320 are subsections of a conduit, such as conduit 242 in FIG. 2. Preferably, conduit subsections 310 and 320 are mateably configured and coupled with one another by the annular housing subsection 330. It is noted that reference to the conduit of the present invention within this disclosure should be interpreted to span across all conduit subsections, so that a first end of the conduit can be on one subsection, while the second end of the conduit can be on a different subsection. In a preferred embodiment, the conduit subsections 310 and 320 are substantially cylindrical in shape, having a constant inner diameter 311, preferably equal to approximately 2 inches. The exterior surface of the conduit subsection 310 can include the feature 314 configured to mate with the annular housing subsection 330. In a preferred embodiment, mating feature 314 is an indentation formed circumferentially around the conduit. Furthermore, the conduit subsection 310 can include a chamfered end 316. The chamfered end 316 is configured opposite of the oppositely chamfered end 326 of the conduit subsection 320. The chamfered ends 316 and 326 preferably form a channel 360 between the two. The conduit subsection 320 can also include a feature 324, similar to feature 314, configured to mate with the annular housing subsection 330. In a preferred embodiment, both the inner and outer surfaces of the two conduit subsections 310 and 320 are substantially similar.

The annular housing subsection 330 can include a relieved portion 334 configured to form a fluid supply chamber 340 when the annular housing subsection 330 mates with the conduit subsections 310 and 320. Preferably, the mating between the conduit subsections 310, 320 and the annular housing subsection 330 is accomplished by a press fit, a friction fit or other similar means. The fluid supply chamber 340 is preferably arranged circumferentially around the conduit subsections 310, 320 and configured to communicate fluidly with the channel 360. Furthermore, the annular housing subsection 330 preferably includes the fluid supply port 332 for supplying conditioning fluid therethrough to the fluid supply chamber 340. Preferably, a conditioning fluid reservoir (not shown) supplies conditioning fluid to the fluid supply port 332 and therethrough to the fluid supply chamber 340, wherefrom the conditioning fluid is drawn into the fluid delivery channels 360 and through the conduit structure containing the conduit coupler 300.

Figure 4:
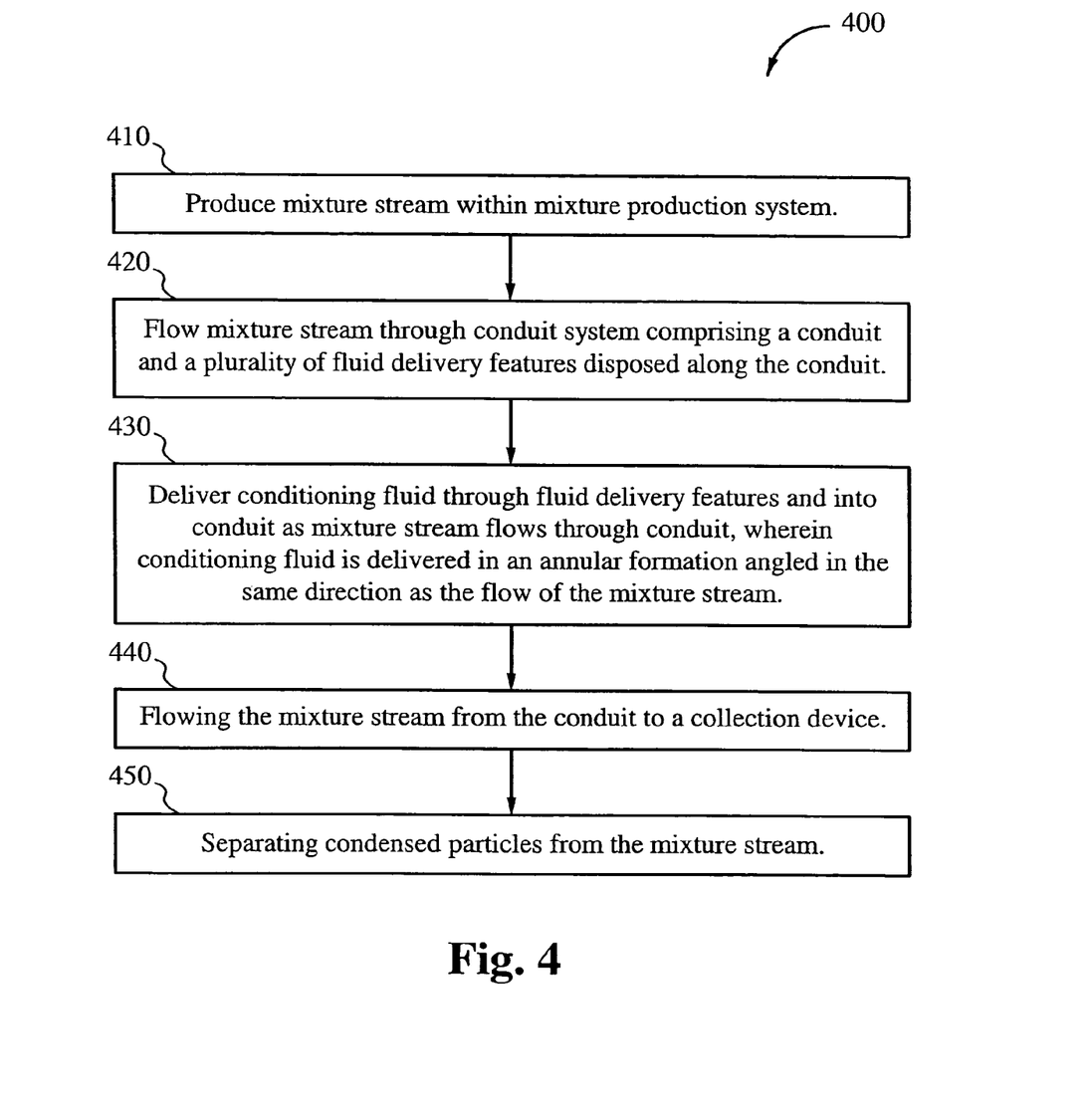
FIG. 4 is a flowchart illustrating one embodiment of a method of conditioning a reactive mixture in accordance with the principles of the present invention.

As can be seen in FIGS. 3 and 4, the port structures 214, 224 and 234 and the delivery channels 360 are preferably configured to deliver the conditioning fluid into the conduit in a direction angled towards the second end in the same direction as the flow of the mixture stream. Additionally, these structures and channels are configured to deliver the conditioning fluid into the conduit in an annular formation. In order to achieve this annular formation, each port structure can include a plurality of supply ports disposed in an annular formation around the conduit. Alternatively, each port structure can include one continuous port disposed circumferentially in the surface of the conduit in order to completely surround the flow of the mixture stream at the point at which the mixture stream passes the port structure. In a preferred embodiment, this continuous port configuration makes the use of the annular housing 330 necessary in order to couple the conduit subsections together.

The arrows 322 illustrate the flow of the gas-particle mixture through the conduit coupler 300. As shown, the flow is constricted near the fluid delivery channels 360 by the symmetric delivery of conditioning fluid into the coupler 300.

FIG. 4 is a flowchart illustrating one embodiment of a method 400 of conditioning a reactive mixture in accordance with the principles of the present invention. As would be appreciated by those of ordinary skill in the art, the protocols, processes, and procedures described herein may be repeated continuously or as often as necessary to satisfy the needs described herein. Additionally, although the steps of method 400 are shown in a specific order, certain steps may occur simultaneously or in a different order than is illustrated. Accordingly, the method steps of the present invention should not be limited to any particular order unless either explicitly or implicitly stated in the claims.

At step 410, a mixture production system, such as the gas-particle mixture production system discussed above, produces a mixture stream. It is contemplated that the mixture stream can be produced in a variety of ways. However, in a preferred embodiment, energy is delivered to a working gas, thereby forming a plasma stream. The plasma stream is then applied to a precursor materia, such as powder particles. The powder is preferably vaporized and the mixture stream is formed, preferably comprising vaporized particles entrained therein.

At step 420, the mixture stream flows to and through a conduit system. The conduit system preferably comprises a conduit formed by a surface extending from a first end to a second end. A plurality of fluid delivery features are preferably disposed along the conduit between the first end and the second end. The mixture stream flows through the conduit from the first end to the second end. It is contemplated that the mixture stream can be partially cooled and that vaporized particles may have already been partially or completely condensed prior to introduction into the conduit.

At step 430, a conditioning fluid is delivered into the conduit while the mixture stream flows through the conduit. The conditioning fluid is delivered through the plurality of delivery features. Each fluid delivery feature delivers the conditioning fluid into the conduit in an annular formation in a direction angled towards the second end in the same direction as the flow of the mixture stream, preferably providing a sheath of conditioning fluid between the conduit surface and the mixture stream.

At step 440, the mixture stream flows from the conduit to a collection device. In a preferred embodiment, the mixture stream at this point has been sufficiently cooled so that the particles have condensed.

At step 450, the mixture stream flows through the collection device and the collection device separates condensed particles from the mixture stream. As previously discussed, this separation can be achieved in a variety of ways.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A conduit system comprising:
   a conduit formed by a surface extending from a first end to a second end, wherein the conduit is configured to channel a mixture stream from the first end to the second end;
   a plurality of fluid delivery features disposed along the conduit between the first end and the second end, wherein each fluid delivery feature is configured to deliver a conditioning fluid into the conduit in an annular formation in a direction angled towards the second end in the same direction as the flow of the mixture stream, thereby providing a sheath of conditioning fluid between the conduit surface and the mixture stream, wherein each fluid delivery feature comprises:

a port structure fluidly coupled to the interior of the conduit and to deliver the conditioning fluid into the conduit in an annular formation in a direction angled towards the second end in the same direction as the flow of the mixture stream, and an annular housing disposed around the conduit and covering the port structure, wherein the annular housing comprises a fluid supply port configured to supply the conditioning fluid to the port structure for delivery into the conduit.

2. The conduit system of claim 1, wherein the annular housing further comprises a fluid supply chamber formed between the fluid supply port and the port structure, the fluid supply chamber disposed circumferentially around conduit and the port structure, the fluid supply chamber being configured to receive the conditioning fluid from the fluid supply port and supply the conditioning fluid circumferentially around and into the port structure.

3. The conduit system of claim 1, wherein each port structure comprises a plurality of fluid subports disposed in an annular formation around the conduit.

4. The conduit system of claim 1, wherein each port structure comprises one continuous fluid port disposed in an annular formation around the conduit.

5. The conduit system of claim 4, wherein the conduit comprises conduit subsections formed between each port structure and adjacent conduit subsections are coupled together by one of the annular housings.

6. The conduit system of claim 5, wherein each fluid delivery feature further comprises an indentation disposed circumferentially in the conduit, the indentation being configured to receive the annular housing and allow the annular housing to mate with the conduit.

7. The conduit system of claim 1, wherein the conduit has a substantially constant diameter of approximately 2 inches.

8. The conduit system of claim 1, wherein the first end of the conduit is fluidly coupled to a mixture production system, the mixture production system being configured to produce the mixture stream, the mixture stream comprising particles entrained within fluid.

9. The conduit system of claim 8, wherein the mixture production system is configured to produce the mixture stream by applying a plasma stream to a plurality of particles, thereby vaporizing the particles.

10. The conduit system of claim 8, wherein a sampling device is fluidly coupled to the second end of the conduit and is configured to receive the mixture stream from the second end of the conduit and separate condensed particles from the mixture stream.

11. A method of conditioning a mixture stream, the method comprising:
providing a conduit formed by a surface extending from a first end to a second end, wherein a plurality of fluid delivery features are disposed along the conduit between the first end and the second end, and wherein each fluid delivery feature comprises a port structure fluidly coupled to the interior of the conduit and an annular housing disposed around the conduit and covering the port structure, the annular housing comprising a fluid supply port;

flowing the mixture stream through the conduit from the first end to the second end; and delivering a conditioning fluid into the conduit while the mixture stream flows through the conduit, wherein the conditioning fluid is flown through the fluid supply port of the annular housing to the port structure where it is delivered through the port structure of each of the delivery features disposed along the conduit between the first end and the second end, each fluid delivery feature delivering the conditioning fluid into the conduit in an annular formation in a direction angled towards the second end in the same direction as the flow of the mixture stream, thereby providing a sheath of conditioning fluid between the conduit surface and the mixture stream.

12. The method of claim 11, wherein the conditioning fluid is an inert gas.

13. The method of claim 11, wherein the annular housing further comprises a fluid supply chamber formed between the fluid supply port and the port structure, the fluid supply chamber disposed circumferentially around conduit and the port structure, the method further comprising the steps of:
the fluid supply chamber receiving the conditioning fluid from the fluid supply port; and
the fluid supply chamber supplying the conditioning fluid circumferentially around and into the port structure.

14. The method of claim 11, wherein each port structure comprises a plurality of fluid subports disposed in an annular formation around the conduit.

15. The method of claim 11, wherein each port structure comprises one continuous fluid port disposed in an annular formation around the conduit.

16. The method of claim 15, wherein the conduit comprises conduit subsections formed between each port structure and adjacent conduit subsections are coupled together by one of the annular housings.

17. The method of claim 16, wherein each fluid delivery feature further comprises an indentation disposed circumferentially in the conduit, the indentation being configured to receive the annular housing and allow the annular housing to mate with the conduit.

18. The method of claim 11, wherein the conduit has a substantially constant diameter of approximately 2 inches.

19. The method of claim 11, wherein the first end of the conduit is fluidly coupled to a mixture production system and the method further comprises the step of the mixture production system producing the mixture stream, the mixture stream comprising particles entrained within fluid.

20. The method of claim 19, wherein the mixture production system produces the mixture stream by applying a plasma stream to a plurality of particles, thereby vaporizing the particles.

21. The method of claim 19, wherein a sampling device is fluidly coupled to the second end of the conduit and the method further comprises the steps of:
the sampling device receiving the mixture stream from the second end of the conduit; and
the sampling device separating condensed particles from the mixture stream.

* * * * *